US008055353B2

(12) United States Patent
Kreidler et al.

(10) Patent No.: US 8,055,353 B2

(45) Date of Patent: Nov. 8, 2011

(54) MEDICAL CARRIERS COMPRISING A LOW-IMPEDANCE CONDUCTOR, AND METHODS OF MAKING AND USING THE SAME

(75) Inventors: Marc Kreidler, Sunnyvale, CA (US); David Huynh, Milpitas, CA (US); Marc Jensen, Los Gatos, CA (US)

(73) Assignee: Proteus Biomedical, Inc., Redwood City, CA (US)

( * ) Notice: Subject to any disclaimer, the term of this patent is extended or adjusted under 35 U.S.C. 154(b) by 219 days.

(21) Appl. No.: 12/370,494

(22) Filed: Feb. 12, 2009

(65) Prior Publication Data

US 2009/0204183 A1 Aug. 13, 2009

Related U.S. Application Data

(60) Provisional application No. 61/028,055, filed on Feb. 12, 2008.

(51) Int. Cl.
*A61N 1/00* (2006.01)

(52) U.S. Cl. ........................................................ 607/122

(58) Field of Classification Search .................... 29/854; 600/373, 374, 504, 435; 607/102, 116, 122, 607/129, 130.17, 48, 59, 72; 381/328
See application file for complete search history.

(56) References Cited

U.S. PATENT DOCUMENTS

| | | | | |
|---|---|---|---|---|
| 3,823,253 | A * | 7/1974 | Walters et al. | 174/69 |
| 5,016,808 | A | 5/1991 | Heil, Jr. et al. | |
| 5,358,517 | A * | 10/1994 | Pohndorf et al. | 607/116 |
| 5,483,022 | A | 1/1996 | Mar | |
| 6,473,512 | B1 * | 10/2002 | Juneau et al. | 381/328 |
| 6,717,056 | B2 | 4/2004 | Rivelli et al. | |
| 7,214,189 | B2 | 5/2007 | Zdeblick | |
| 7,265,298 | B2 * | 9/2007 | Maghribi et al. | 174/254 |
| 2002/0060289 | A1 * | 5/2002 | Cornish et al. | 250/281 |
| 2004/0193021 | A1 | 9/2004 | Zdeblick et al. | |
| 2006/0241422 | A1 * | 10/2006 | Muratayev et al. | 600/435 |
| 2008/0129465 | A1 * | 6/2008 | Rao | 340/286.02 |
| 2008/0147155 | A1 * | 6/2008 | Swoyer et al. | 607/116 |
| 2008/0228252 | A1 * | 9/2008 | Westlund et al. | 607/130 |
| 2008/0255647 | A1 | 10/2008 | Colliou et al. | |
| 2008/0300449 | A1 * | 12/2008 | Gerber et al. | 600/30 |

* cited by examiner

*Primary Examiner* — George Manuel
*Assistant Examiner* — Robert N Wieland
(74) *Attorney, Agent, or Firm* — Bozicevic, Field & Francis LLP; Bret E. Field

(57) ABSTRACT

Medical carriers that include a low-impedance conductor are provided. The low-impedance conductors are configured to provide electrical conductivity along a length of the medical carrier. An aspect of the low-impedance conductors is the presence of a longitudinally extended region configured as a non-coiled repetitive pattern that imparts fatigue resistance to the longitudinally extended region. Also provided are systems and methods of making the medical carriers, as well as methods of using the medical carriers.

25 Claims, 10 Drawing Sheets

10 11 12 13 14

15 16 17 18 19 19

MEDICAL CARRIERS COMPRISING A LOW-IMPEDANCE CONDUCTOR, AND METHODS OF MAKING AND USING THE SAME

CROSS-REFERENCE TO RELATED APPLICATIONS

Pursuant to 35 U.S.C. §119(e), this application claims priority to U.S. Provisional Application No. 61/028,055, filed on Feb. 12, 2008, the disclosure of which is hereby incorporated by reference.

INTRODUCTION

Various medical devices may include a medical carrier for conveying signals or information from one location to another. Regardless of the particular application for which they are designed, medical carriers are generally elongated flexible structures that include one or more electrical conductors, such as wires, extending along a length of the carrier. Medical carrier conductors can be configured in a variety of different formats. One format that is employed is a linear wire or stranded cable that extends along a length of the carrier. Alternatively, coiled or helical configurations have been employed, where the conductor is positioned in a spiral configuration about the circumference of the carrier.

Medical carriers of the invention may be implantable or non-implantable. Examples of implantable medical carriers include medical electrical leads, such a cardiac stimulation leads and neuro-stimulation leads. Examples of non-implantable medical carriers include medical carriers found in devices which are configured to be introduced into a body for a limited period of time, such as diagnostic and/or surgical devices, including endoscopes and minimally-invasive surgical tools.

SUMMARY

Medical carriers that include a low-impedance conductor are provided. The low-impedance conductors are configured to provide electrical conductivity along a length of the medical carrier. An aspect of the low-impedance conductors is the presence of a longitudinally extended region configured as a non-coiled repetitive pattern that imparts fatigue resistance to the longitudinally extended region. Also provided are systems and methods of making the medical carriers, as well as methods of using the medical carriers.

BRIEF DESCRIPTION OF THE DRAWINGS

FIG. 6 shows a drawing of an embodiment of a low-impedance conductor where the width of the low-impedance conductor varies along its length.

DETAILED DESCRIPTION

Figure 1A:
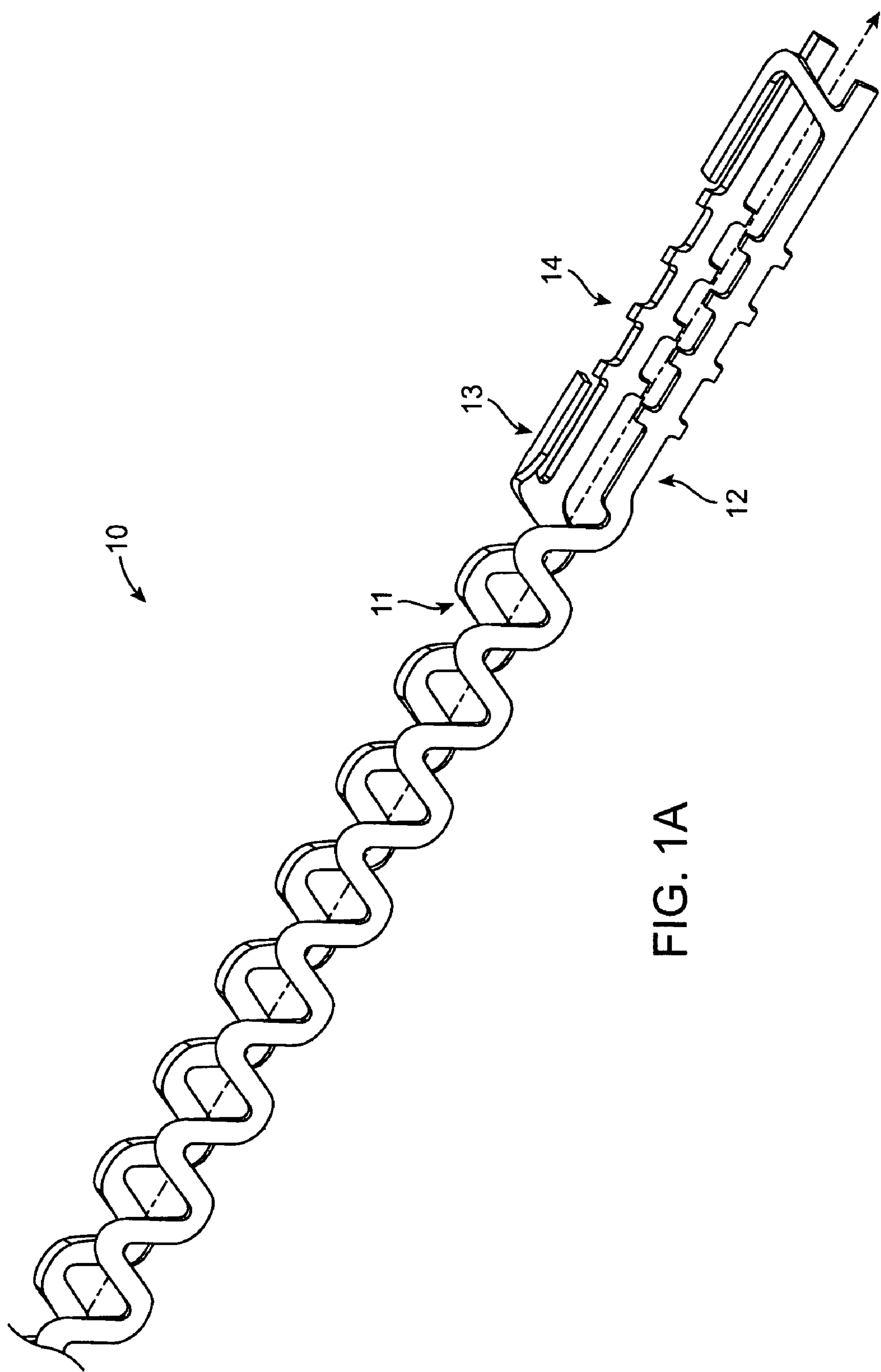
FIG. 1A shows an embodiment of a low-impedance conductor that includes a flexible longitudinally extended region configured as a sinusoidal wave pattern.

Medical carriers that include a low-impedance conductor are provided. The low-impedance conductors are configured to provide electrical conductivity along a length of the medical carrier. An aspect of the low-impedance conductors is the presence of a longitudinally extended region configured as a non-coiled repetitive pattern that imparts fatigue resistance to the longitudinally extended region. Also provided are systems and methods of making the medical carriers, as well as methods of using the medical carriers.

Low-Impedance Medical Carriers

Medical carriers of the invention include a low-impedance conductor. As used herein, the term "medical carrier" refers to an elongated medical device configured to be used with an animal, such as a mammal, such as a human. Medical carriers of the invention are flexible structures that may be configured to be inserted into a body or implanted in a body for some duration of time. As the medical carriers are elongated, they have a length that is 1.5 times or longer than their width, such as 2 times or longer than their width, including 5 or 10 times longer than their width, such as 20 times longer than their width, 30 times longer than their width, etc. In some instances, the medical carriers have a length ranging from 10 to 120 cm, such as 80-110 cm and a width ranging from 3 to 12 Fr, such as 8 to 10 Fr. Medical carriers of the invention may be implantable or non-implantable. Examples of implantable medical carriers include medical electrical leads, such a cardiac stimulation leads and neuro-stimulation leads. Examples of non-implantable medical carriers include medical carriers found in devices which are configured to be introduced into a body for a limited period of time, such as diagnostic and/or surgical devices, including endoscopes and minimally-invasive surgical tools. In one example, endoscopes may be up to 0.75 inches in diameter.

As summarized above, medical carriers of the invention include one or more low-impedance conductors of the invention. The low-impedance conductors present in the medical carriers are conductors that are configured to provide electrical conductivity along a length of the medical carrier. By providing electrical conductivity along a length of the medical carrier, the low-impedance conductors provide for transmission of power and/or data along a length of the medical carrier with which they are associated. By "along a length" is meant that the electrical conductivity is provided over a distance (in other words, from a first point to a second point) along the medical carrier, and is not confined to one location of the medical carrier. For example, the low-impedance conductor may provide for electrical conductivity for a distance along the medical carrier of 10 mm or greater, such as 50 mm or greater, including 100 mm or greater, for example 250 mm or greater. In some cases, the low-impedance conductor provides for electrical conductivity for a distance of 250 mm or less, such as 100 mm or less, including 50 mm or less.

Low-impedance conductors of the invention are configured to provide for one or more of a number of different desirable characteristics, including one or more of high fatigue resistance, flexibility, adaptability, low impedance and compact geometry (to maximize real-estate available in the medical carrier for other purposes). Low-impedance conductors of the invention include a longitudinally extended region. By "longitudinally extended region" is meant a region that extends for a length along the medical carrier. While lengths of this longitudinally extended region may vary, in some instances the longitudinally extended region ranges in length from 10 mm to 250 mm, such as 10 to 100 mm, including 10 to 50 mm. The longitudinally extended region can have a variety of shapes or conformations. The dimensions of the longitudinally extended region of the low-impedance conductor may vary depending on the particular medical carrier for which the low-impedance conductor is configured. In some instances, the thickness of the low-impedance conductor is selected in view of the desired current density (which may be required to power a device that includes the medical carrier) as well as the desired impedance for optimal signal propagation given a certain drive frequency. In some instances, the low-impedance conductor has a substantially rectangular cross-sectional configuration, which may be described by thickness and width. The cross-sectional area of subject low-impedance conductors may vary, where in some instances the cross-section area may range from 0.2 to 1.5 $mm^2$, such as 0.5 to 0.7 $mm^2$. For such low-impedance conductors, the thickness of the low-impedance conductor may range from 0.002 mm to 10 mm, such as from 0.01 mm to 1 mm, and including from 0.02 mm to 0.4 mm, while the width of the low-impedance conductor may range from 0.01 mm to 1000 mm, such as from 0.1 mm to 100 mm, and including from 0.4 mm to 30 mm. Where the longitudinally extended region is curved around a longitudinal axis, as described in greater detail below, the diameter of a circle defined at least partially by longitudinally extended region can range from 0.01 mm to 1000 mm, such as from 0.1 mm to 100 mm, and including from 0.25 mm to 20 mm.

Longitudinally extended regions of the low-impedance conductors are configured as a non-coiled repetitive pattern that imparts fatigue resistance to the longitudinally extended region. As the longitudinally extended region has a non-coiled configuration, the longitudinally extended region is not configured in the shape of a coil. As such, the longitudinally extended region is not configured as a spiral, such that the longitudinally extended region may not be described as a coiling around a fixed line or axis in a constantly changing series of planes. Accordingly, the longitudinally extended region does not have a helical configuration.

The longitudinally extended region is configured to include a repetitive non-linear pattern that imparts fatigue resistance to the longitudinally extended region. As the low-impedance conductors exhibit fatigue resistance, the low-impedance conductors exhibit resistance to cumulative damage which accrues in response to repetitive bending, compression, elongation or analogous forces. This fatigue resistance ensures that the low-impedance conductors can survive intact in an in vivo environment (such as in a physiological environment) without substantial, if any, breakage. For example, where the low-impedance conductors are present in lead which is configured to be associated with cardiac tissue, the low-impedance conductors may exhibit a fatigue limit from 24 hours to 10 years or more of survival in the body, such that they are configured to survive between 86,000 to 315,000,000 cycles of heart beats without undergoing fatigue failure (as evidenced by a substantial decrease in functionality, such as ability to conduct an electrical signal).

As summarized above, the longitudinally extended region is configured to include a repetitive pattern. By repetitive pattern is meant a configuration made up of one or more repeating structural units. The frequency of the repetitive pattern may vary as desired, where in some instances the frequency of the repetitive pattern ranges from 0.05 to 20 mm, such as 0.05 to 5 mm and including 0.05 to 0.1 mm, where higher frequencies may be chosen to provide for increased flexibility and fatigue resistance. While the repetitive pattern of a given longitudinally extended region may vary, in some instances the repetitive pattern is a pattern selected from the group consisting of a sinusoidal wave, triangle wave, square wave or irregular wave pattern. A sinusoidal wave is a repetitive wave pattern whose amplitude varies in proportion to the sine of a variable, such as distance or time. A triangle wave is a repetitive wave pattern whose amplitude increases up to a first level and then decreases down to a second level, such that the wave pattern has a triangle shape. A square wave is a repetitive wave pattern whose amplitude alternates regularly between two levels, such that the wave pattern has a square shape. An irregular wave pattern is a wave pattern whose shape may be definable as a waveform such as, but not limited to, a waveform made up of periods that have varying frequencies, a waveform made up of periods that have varying amplitudes, a waveform made up of periods that have varying frequencies and varying amplitudes, a superposition of two or more waveforms, and the like.

The structural features of the longitudinally extended region, such as the sinusoidal or wavy pattern described above, impart fatigue resistance to the longitudinally extended region. In some embodiments, the low-impedance conductor has a fatigue life from $10^2$ to $10^9$ cycles, such as from $3\times10^6$ to $10^9$ cycles and including from $3\times10^6$ to $4\times10^8$ cycles of repeated stress without having significant fatigue failure. As used herein, the terms "fatigue" and "metal fatigue" refer to the progressive and localized structural damage that occurs when a material is subjected to repeated stress. The non-coiled repetitive pattern of the longitudinally extended region allows for more give when the conductor is under strain, compressive stress or bending. In certain cases, the low-impedance conductor includes a bending stiffness ranging from 1 gram/cm per radian to 454 grams/cm per radian, such as from 1 gram/cm per radian to 90 grams/cm per radian, and including from 1 gram/cm per radian to 10 grams/cm per radian. In addition, the low-impedance conductor may exhibit a stretch ratio (in other words, an elongation ratio) from 0.2% to 20%, such as from 0.5% to 10%, including from 1% to 5%.

The bending stiffness may vary along the length of the low-impedance conductor. In certain cases, the bending stiffness varies linearly along the length of the low-impedance conductor, such as but not limited to, increasing linearly towards the distal end of the low-impedance conductor, decreasing linearly towards the distal end of the low-impedance conductor, increasing and decreasing at various positions along the length of the low-impedance conductor, and the like. In some instances, the bending stiffness varies non-linearly along the length of the low-impedance conductor. The bending stiffness of the longitudinally extended region can be changed during fabrication of the conductor by varying the radius of curvature of the repetitive pattern (as described in greater detail below), the frequency of the repetitive pattern, the cross-sectional areas of the repetitive pattern, and the like. This allows the bending stiffness along the length of the low-impedance conductor to be tailored to suit various applications, as needed. For example, the distal end of a medical carrier may require higher flexibility for maneuvering through certain areas in the body, while other parts of the medical carrier may need to be stiffer. Where desired, a repetitive pattern with a high frequency of bends can be designed into the low-impedance conductor near the distal end while a repetitive pattern with a low frequency of bends and a high radius of curvature can be designed into the proximal end. This adaptability of design allows for different regions along the length of the conductor to be configured to have different bending stiffnesses.

As compared to a coiled conductor, the non-coiled repetitive pattern of the low-impedance conductors of the invention decreases the volume of the conductors, decreases the electric path length of the low-impedance conductors and consequently the resistance of the low-impedance conductors. As such, the configuration lowers the inductance of the low-impedance conductors. The configuration of the non-coiled repetitive pattern provides for these qualities by not requiring the extra length of conductive material to wind around the entire circumference of the medical carrier, as with a coiled conductor, but rather includes sinusoidal, wavy or other repetitive fatigue resistant patterns on only a portion of the circumference of the medical carrier.

Decreasing the electric path length of the conductor consequently decreases the resistance of the conductor. The phrase "electrical resistance" is employed in its conventional sense to refer to a ratio of the degree that a conductor opposes an electric current through it. The total resistance of a conductor is its resistivity multiplied by the length of the electric path. Lower resistance equates to higher conductance since the resistance is inversely proportional to conductance. In addition, resistance is also linearly proportional to power dissipation. Thus, a lower resistance will decrease the power dissipation along the length of the conductor. A conductor with less power loss is more efficient in transmitting power along the length of the conductor, thus the overall power consumption of a device can be decreased. The non-coiled repetitive pattern of the subject low-impedance conductors decreases the electric path length of the conductors as compared to coiled conductors. By decreasing the electric path length, the non-coiled repetitive pattern consequently lowers the total resistance of the low-impedance conductors. Depending on the materials from which they are fabricated, the low-impedance conductor may exhibit a resistance ranging from 0.01 Ω/cm to 5 Ω/cm, such as 0.04 Ω/cm to 5 Ω/cm, and including 0.4 Ω/cm to 2 Ω/cm.

As discussed above, the non-coiled repetitive pattern of the low-impedance conductors lowers the inductance of the low-impedance conductors relative to coiled conductor configurations. "Inductance" is used in the conventional sense to refer to a property in a conductor where a change in the current flowing through the conductor induces an electromotive force (EMF) that opposes the change in current. Coiled conductors can be highly inductive. By avoiding such geometry in favor of the configurations of the subject low-impedance conductors, such as sinusoidal, wavy or other fatigue resistant patterned conductors, the configuration of the subject low-impedance conductors facilitates a lower inductance relative to coiled conductors. Thus, higher conductance coupled with lower inductance results in a decrease in signal delay of high-frequency transmissions across the low-impedance conductors, for example as compared to coiled conductors. The lower inductance for the low-impedance conductors, in conjunction with the lower resistance, as described above, results in lower impedance of the conductor, for example as compared to a comparable coiled conductor. "Impedance" is employed in its conventional sense to describe a measure of opposition to a sinusoidal alternating current (AC). Electrical impedance extends the concept of resistance to AC circuits, describing not only the relative amplitudes of the voltage and current, but also the relative phases. Thus, the non-coiled repetitive pattern of the subject conductors provides for lower impedance relative to coiled conductors.

Where desired, the longitudinally extended region of the low-impedance conductors may be configured to be curved about a longitudinal axis. For such low-impedance conductors, the longitudinally extended region of the conductor will have a curved surface. In some cases, the curved surface may be described in terms of its radius of curvature, where the curved surface may have a radius of curvature of 10 mm or less, including 5 mm or less, for example 3 mm or less, such as 2 mm or less, including 1 mm or less about the longitudinal axis. Since the longitudinally extended region is curved about the longitudinal axis, the cross-section of the longitudinally extended region has an arc configuration about the longitudinal axis. In some instances, the longitudinally extended region fully encircles the longitudinal axis (such that its cross-sectional shape may be defined as an arc of 360 degrees). In other embodiments, the longitudinally extended region is made up of only a portion of a complete 360 degree arc about the longitudinal axis. Thus, the cross-sectional shape of the longitudinally extended region can be described as an arc of 360 or less, such as 270 degrees or less, including 180 degrees or less, for example 90 degrees or less about the longitudinal axis.

The curved, arc-shaped longitudinally extended region can define all, or a portion of the circumference of a tubular structure. In some cases, the longitudinally extended region is positioned on the outer periphery of the medical carrier. In these cases, the longitudinally extended region comprises a structure that defines a central lumen surrounded (at least partially) by the curved, arc-shaped longitudinally extended region. This type of structure conserves space within the medical carrier by positioning the longitudinally extended region of the low-impedance conductor towards the outer periphery of the medical carrier. In certain embodiments, the longitudinally extended region comprises 75% or less, such as 50% or less, including 25% or less, for example 10% or less of the cross-sectional area of the medical carrier in the portion of the medical carrier in which the longitudinally extended region is present.

Where desired, the central lumen of the medical carrier may be hollow (such that it includes a void) and may be surrounded at least partially by the longitudinally extended region of the low-impedance conductors, as described above. Alternatively, the central lumen of the medical carrier may include any of a variety of other structures or devices, such as, but not limited to, additional conductive elements, optical fibers, cables, mechanical actuators, and the like, depending on the purpose for which the medical carrier is configured. In addition, the central lumen can comprise an insulator, such as a polymeric insulator. Thus, in certain embodiments, the low-impedance conductor can surround a polymeric insulator that insulates the conductor from other components, such as conductive members, that may be present in the lumen of the medical carrier. The polymer can be configured as a tubular structure (such as a hollow cylinder), a solid cylindrical structure, a porous structure, etc., as desired.

In some medical carriers of the invention, the longitudinally extended region of the low-impedance conductor is positioned at the distal end of the low impedance conductor. By distal end is meant the end of the conductor closest to the target tissue location in the body of the subject when the medical carrier is in use. In contrast, the proximal end of the low-impedance conductor refers to the end of the low-impedance conductor further away from the target location in the body of the subject when the medical carrier is in use. In some cases, the longitudinally extended region is positioned between the proximal end and the distal end of the conductor. Thus, the conductor can be configured to include one or more longitudinally extended regions, where the longitudinally extended regions are positioned at various locations along the length of the conductor.

Where desired, a medical carrier of the invention may include one or more additional conductors that are distinct from any low-impedance conductors of the carrier. For example, the medical carrier may include a second conductor that is electrically coupled to the low-impedance conductor, for example at the proximal end of the low-impedance conductor. This second conductor, when present, may be configured in any desired manner, such as in a conventional linear or coiled manner.

Medical carriers of the invention may include one or more effectors operatively coupled to the low-impedance conductor. The term "effector" is used to refer to a sensor, an actuator, or a sensor/actuator. In some instances, the effector includes one or more electrodes, where, in some cases. Of interest in certain embodiments are segmented electrode effectors that include two or more electrodes coupled to an individually identifiable processor, where such electrodes are further described in PCT Application Serial No. US2005/031559 published as WO 2006/029090, PCT application Serial No. US2005/046811 published as WO 2006/069322 and U.S. application Ser. No. 11/939,524 published as 2008/0114230; the disclosures of which are herein incorporated by reference. Medical carriers of the invention may include a single effector or two or more longitudinally spaced effectors along the length of the conductor, as desired. Where a given medical carrier includes two or longitudinally spaced effectors, the longitudinally spaced effectors can be electrically connected to the low-impedance conductor at various positions along the length of the low-impedance conductor. In some instances the effectors are positioned such that the longitudinally extended region of the low-impedance conductor is positioned between the effectors, for example where the longitudinally extended region is flanked on both sides by an effector.

Medical carriers of the invention may include electrical connectors. Electrical connectors, when present, may have a variety of configurations depending on the desired application. Electrical connectors are elements that form a junction connecting one structure to another such that electricity can be conveyed across the junction. In certain embodiments, the subject medical carrier includes a connector having a proximal end configured to connect to a device. The device can be any of a variety of devices depending on the desired application, such as but not limited to an implantable pulse generator, an extra-corporeal control device, and the like. Connectors of interest include those having an IS-1 designation, indicating they have been manufactured in compliance with ISO standard 5841.3:1992. Also of interest are connectors having a DF-1 designation, indicating they have been manufactured in compliance with ISO standard 11318:1993.

Medical carriers of the invention may include a single low-impedance conductor of the invention or two or more low-impedance conductors of the invention. In some instances, the medical carriers include two conformal low-impedance conductors that are configured to be positioned in medical carrier in a manner that defines a central lumen between the two low-impedance conductors. See for example the medical carriers depicts in FIG. 1A and FIG. 1B.

Figure 1B:
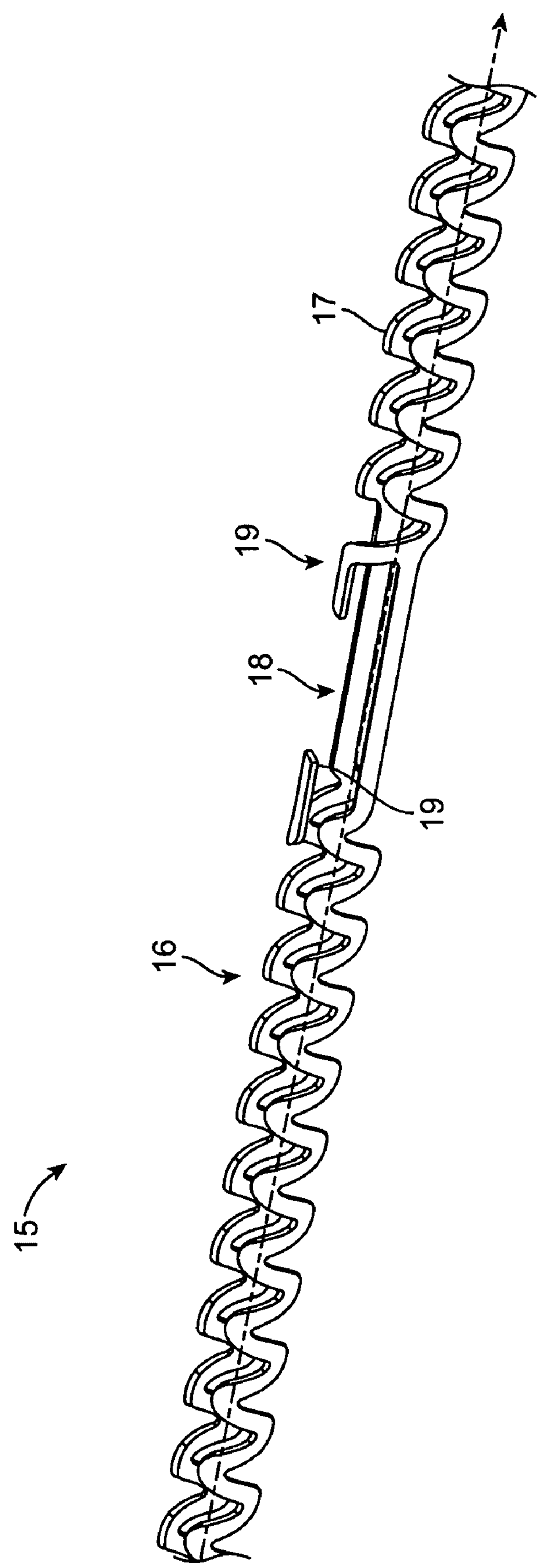
FIG. 1B shows a schematic view of the flexible pattern formed in the low-impedance conductor with connectors and a straight section that coincides with an effector location.

A low-impedance conductor that may be present in a medical carrier of the invention is shown in FIG. 1A. FIG. 1A provides a perspective view of two conformal low-impedance conductors of the invention that may be found in a portion of a medical carrier. In FIG. 1A, low-impedance conductor 10 includes a longitudinally extended region 11 having a non-coiled repetitive pattern, and specifically a sinusoidal pattern. In addition to the longitudinally extended region 11, the low-impedance conductor 10 also includes a substantially linear region 12. Linear region 12 includes connectors 13 configured to provide electrical connection to a processor of a segmented electrode effector. Also shown are elements 14 which provide for structure integrity of bonding. FIG. 1B depicts another pair of conformal low-impedance conductors of the invention. In FIG. 1B, low impedance conductor 15 includes a first longitudinally extended region 16 having a non-coiled repetitive pattern and a second longitudinally extended region 17 that includes a non-coiled repetitive pattern having the same configuration as that of the first non-coiled repetitive pattern, which is a sinusoidal pattern. A substantially straight section 18 is positioned between regions 16 and 17 to occupy minimal space in the region of the medical carrier where an effector, such as a segmented electrode, is to be positioned. Also shown are connectors 19 which are configured to provide electrical connection to an effector when present. This configuration provides a low-profile connection that is more structurally reliable than multiple separate connections.

The low-impedance conductors shown in FIGS. 1A and 1B have longitudinally extended regions that are curved about a longitudinal axis, where the longitudinal axis is designated as a dashed arrow. Because of the design of the low-impedance conductors of the invention, the low-impedance conductors may exhibit a compactness factor in the stacking of conductors. For example, low-impedance conductors of the invention may be configured to provide for cylindrical stacking, and hence increase the efficiency of packing within a defined volume of a medical carrier. The low-impedance conductor also achieves efficiency of space by not requiring the extra length of conductor material to wind around the entire circumference of the medical carrier as in a coiled conductor.

Figure 2A:
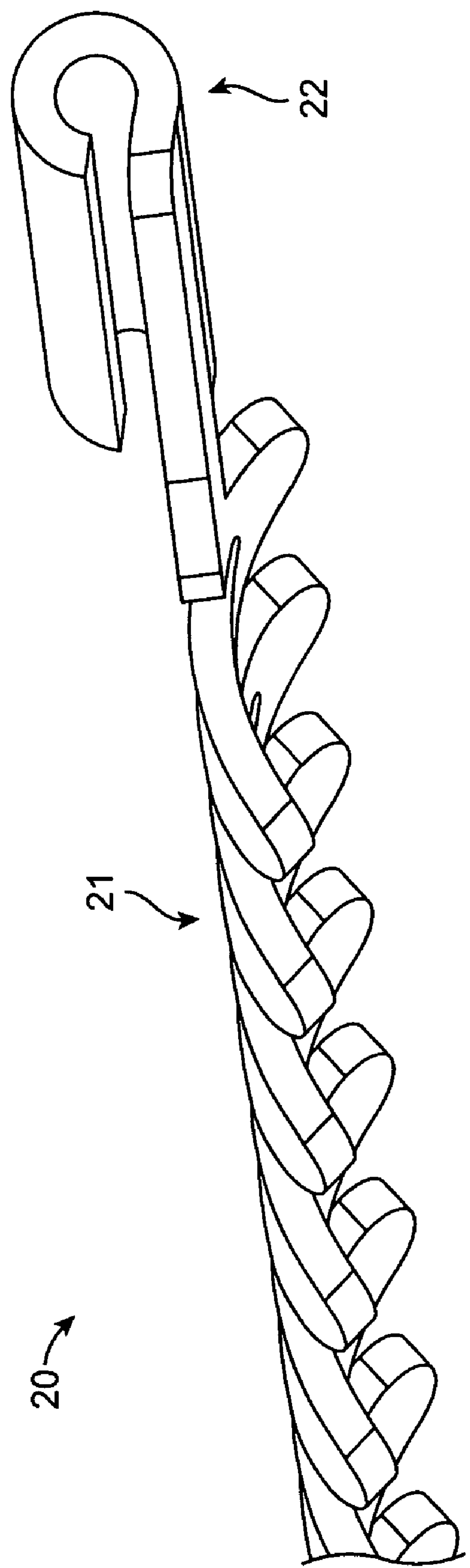
FIG. 2A depicts a low-impedance conductor that includes a connector for connecting the low-impedance conductor to a stranded cable, in accordance with the invention.
Figure 2B:
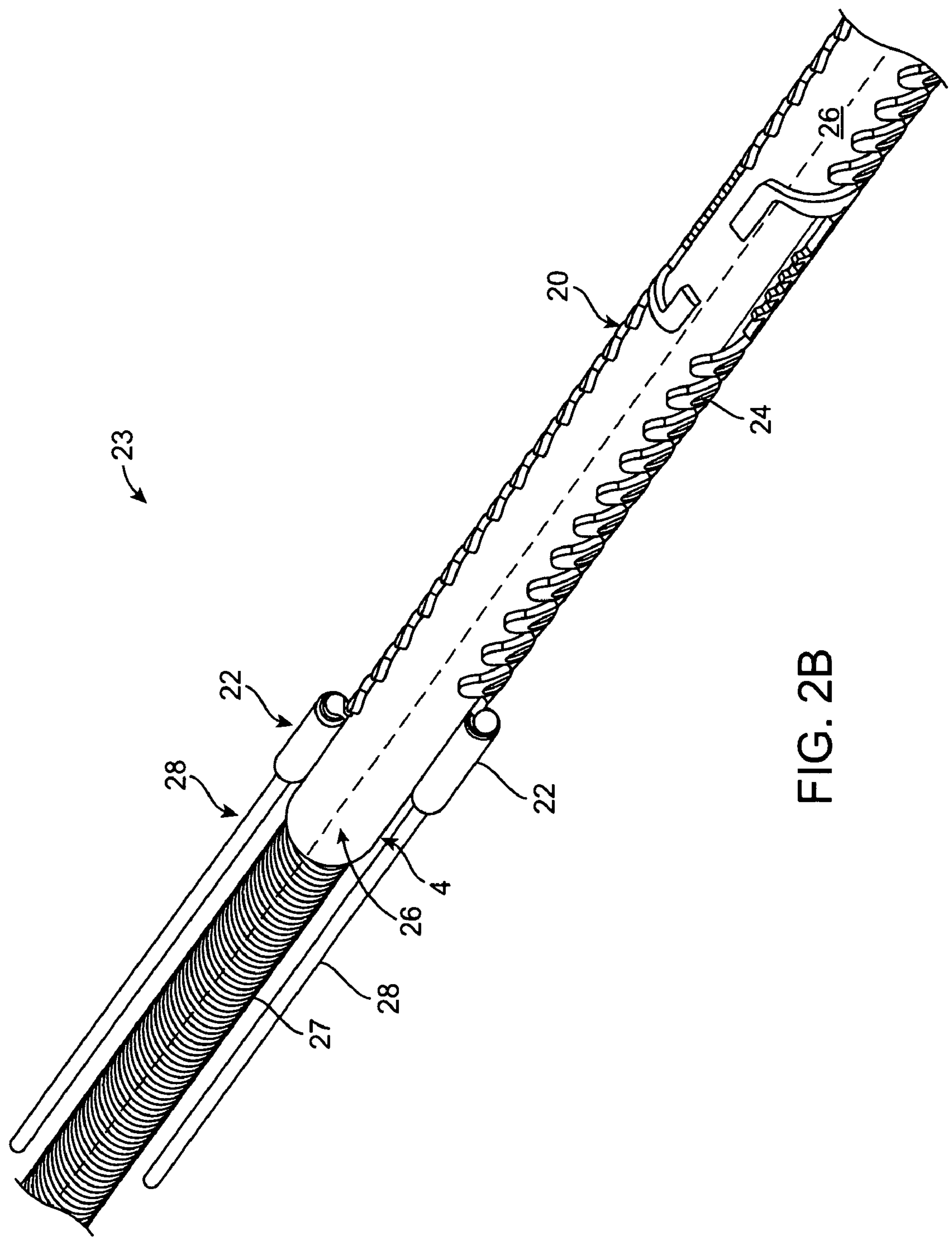
FIG. 2B depicts a connection between the low-impedance conductor and a stranded cable.

As described above, low-impedance conductors of the invention may include connector elements that provide for electrical connection to additional conductors, such as linear or coiled conductors. FIG. 2A shows a view one such low-impedance conductor. In FIG. 2A, low-impedance conductor 20 includes a connector 22 at its proximal end, adjacent to the longitudinally extended region 21 of the low-impedance conductor 20. FIG. 2B provides a cutaway view of a medical carrier 23 of the invention that includes the low-impedance conductor 20 shown in FIG. 2A. In FIG. 2B, medical carrier 23 includes first low-impedance conductor 20 and second low-impedance conductor 24. First and second low-impedance conductors 20 and 24 are curved about a longitudinal axis (shown as a dashed line) and are conformal so as to define a central lumen in the medical carrier, which is occupied by a polymeric sheath 26 covering a helical tube 27. Positioned at the proximal end of each low-impedance conductor are connectors 22 which provide connection with additional conductive elements 28, such as stranded cables 25.

Figure 3:
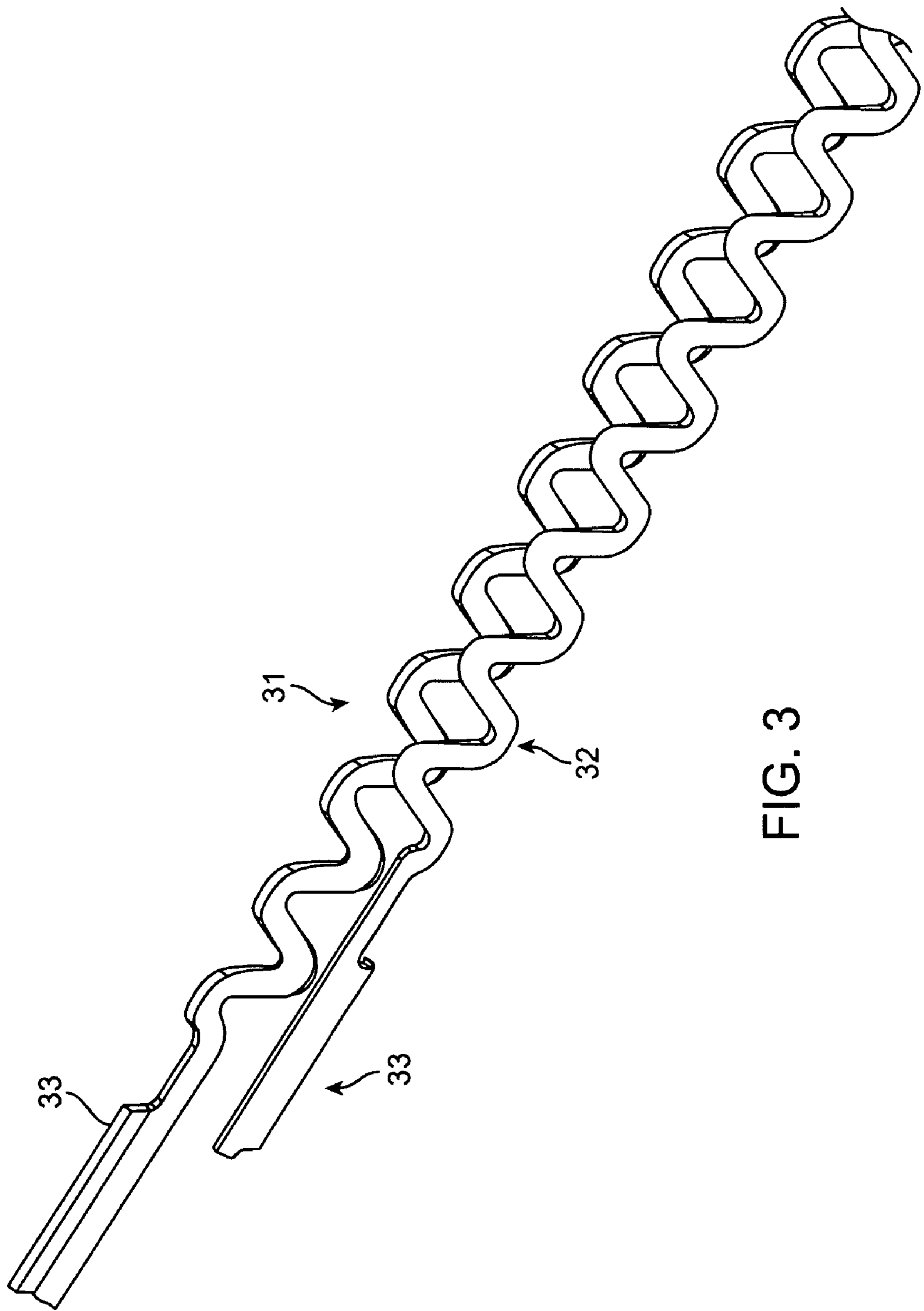
FIG. 3 depicts a distal end of a low-impedance conductor in accordance with the invention.

FIG. 3 provides a depiction of a pair of low-impedance conductors 31 and 32. Located at the distal end of each low-impedance conductor is a formed connector 33. The formed connectors 33 can be embedded into the insulating portions of the medical carrier or they can be exposed to serve as pacing or sensing electrodes. By "exposed", it is meant that a structure is able to contact a target tissue.

Figure 4:
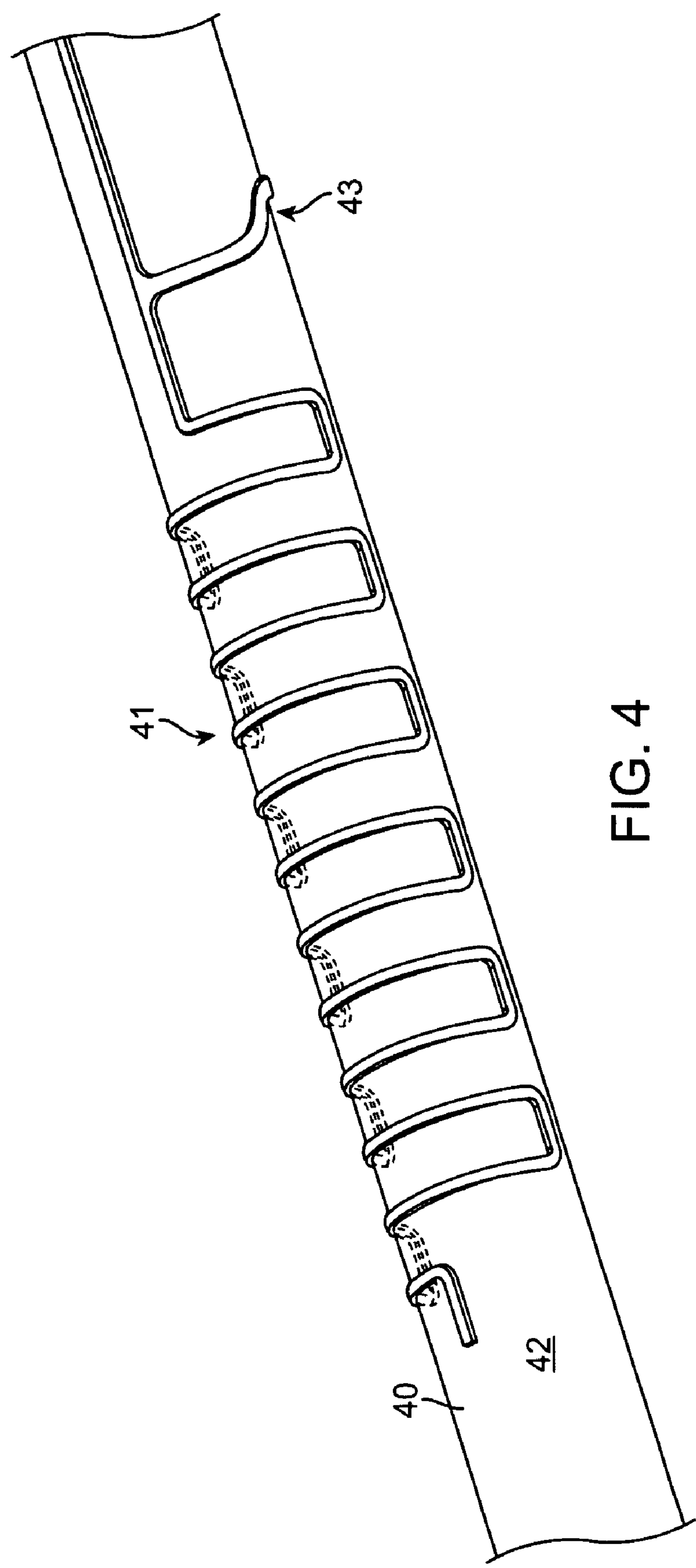
FIG. 4 depicts a medical carrier that includes a low-impedance conductor having a longitudinally extended region that is configured as a square wave pattern.

FIG. 4 depicts a medical carrier 40 with a low-impedance conductor 41 present on an insulating member 42. Low-impedance conductor 41 includes longitudinally extended region 43 which is configured as a square wave pattern. Also shown is connector 43 which can provide for connection to an effector, when present.

Figure 5:
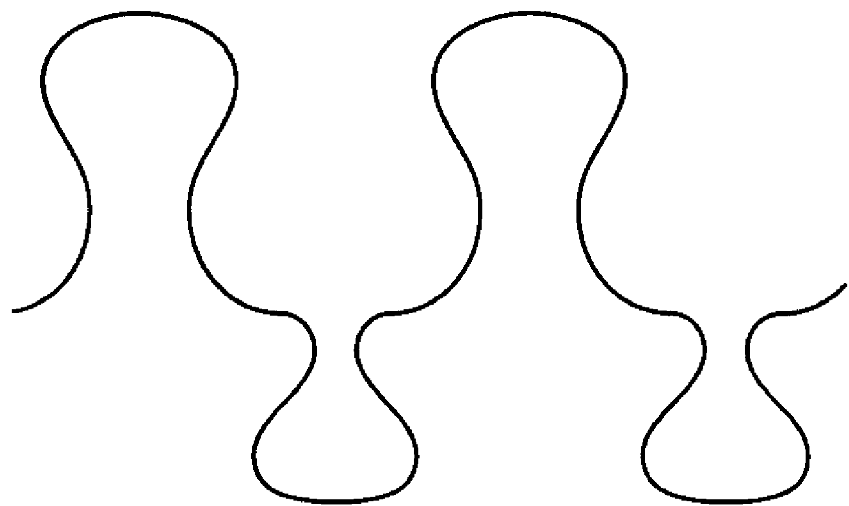
FIGS. 5 and 6 depict irregular repetitive pattern configurations that may be present in longitudinally extended regions of low-impedance conductors of the invention.
Figure 6:
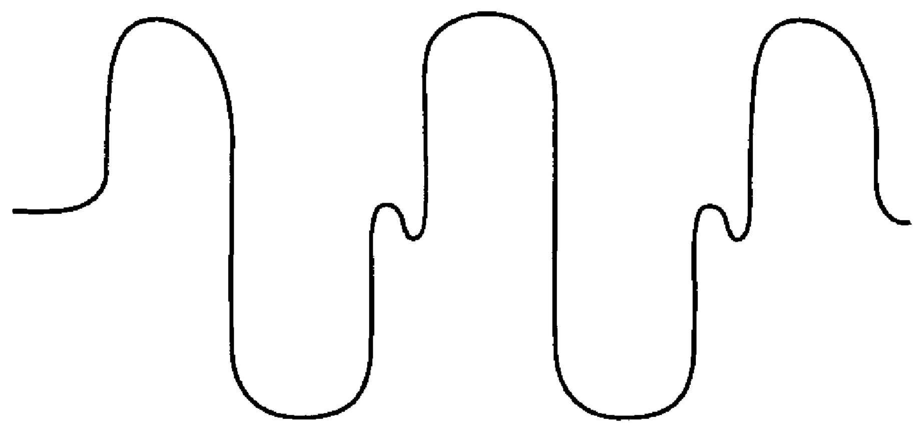

As described above, the longitudinally extended regions of the low-impedance conductors can have a variety of repetitive patterns that impart fatigue resistance to the low-impedance conductor. Patterns of interest include sinusoidal, triangular and square waveform patterns. Also of interest are irregular repetitive patterns. Two examples of irregular patterns of interest are depicted in FIGS. 5 and 6. These patterns may be repeating or they may be varied along the length of the conductor to provide a desired longitudinal flexibility. The shape of the repetitive pattern can also be varied to facilitate fixation of the conductor at a target location in the body of a subject.

Figure 7:
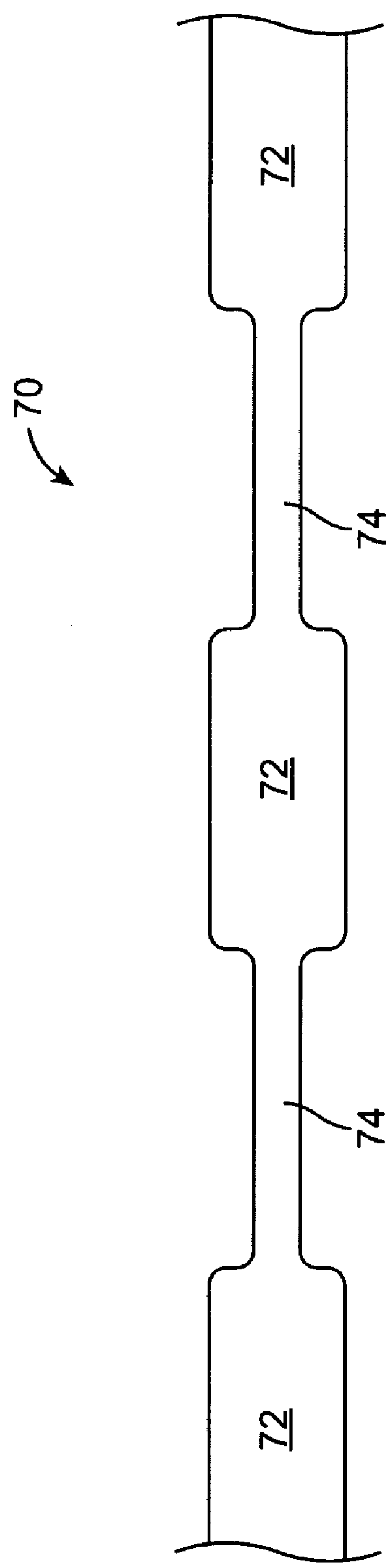
FIG. 7 depicts a low-impedance conductor having regions of varying thickness, in accordance with the invention.

FIG. 7 depicts a low-impedance conductor 70 where the width of the low impedance conductor 70 varies along its length. Specifically, low-impedance conductor 70 includes regions of greater thickness 72 relative to regions of lesser thickness 74. The thickness of various regions and spacing thereof along the length of the low-impedance conductor may be chosen to impart more or less bending stiffness to regions along the length of the low-impedance conductor, as desired.

Figure 8:
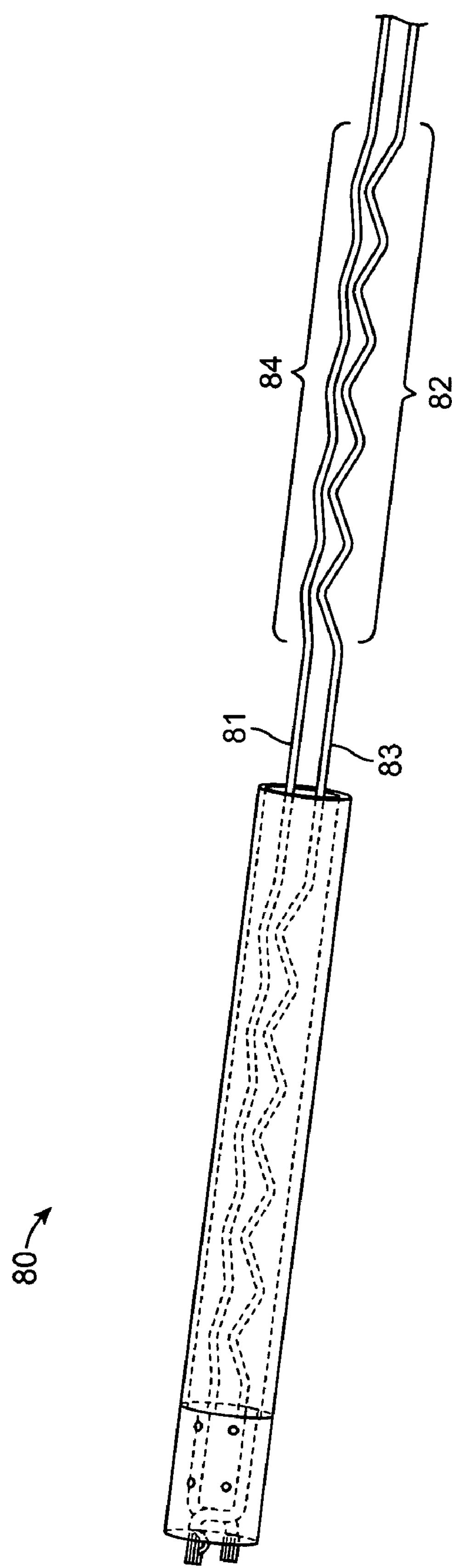
FIG. 8 depicts a medical carrier that includes two low-impedance conductors with longitudinally extended regions that differ from each other in terms of frequency of their repetitive patterns.

An additional configuration of a medical carrier of the invention is depicted in FIG. 8. In FIG. 8, the medical carrier includes two low-impedance conductors 81 and 83. Low-impedance conductors 81 and 83 include longitudinally extended regions 82 and 84 that different from each other with respect to frequency of their repetitive patterns. The different frequency of the repetitive pattern imparts different flexibilities to the low-impedance conductors 81 and 83, which facilitates bending of the medical carrier 80. In this manner, the medical carrier can be configured such that directionality of bending of the medical carrier can be preferentially selected. For example, by including conductors that have different bending stiffnesses, the medical carrier can prefer to bend in one direction versus another direction.

As reviewed above, medical carriers of the invention may be implantable or non-implantable. Examples of implantable medical carriers include medical electrical leads, such a cardiac stimulation leads and neuro-stimulation leads. In some implantable leads of the invention, the medical carrier is dimensioned to be intra-luminally positioned in a body. By "intra-luminally" is meant that the medical carrier is dimensioned to fit within a space in a body, such as an intra-cardiac space, an intra-ocular space, an intra-cranial space, an intra-abdominal space, an intra-vascular space, and the like. For example, the medical carrier can have a diameter ranging from 0.01 mm to 10 mm, such as from 0.1 mm to 8 mm, and including from 0.25 mm to 7 mm. In certain cases, the medical carrier can have a diameter of 7 mm or less, such as 6 mm or less, including 5 mm or less, for example 3 mm or less, such as 2 mm or less, including 1 mm or less. For medical carriers of the invention that are implantable, the medical carriers are structures that may be positioned at a location inside of a body and function without significant, if any, deterioration (for example in the form of breakage of the low-impedance conductor, such as determined by function of the medical carrier) for extended periods of time. As such, once implanted, the medical carriers do not deteriorate in terms of function, for example as determined by function of an integrated circuit and electrodes coupled to the low-impedance conductor of the medical carrier, for a period of at least two or more days, such as at least one week, at least four weeks, at least six months, at least one year or longer, such as at least five years or longer, for example at least ten years or longer. Examples of non-implantable medical carriers include medical carriers found in devices which are configured to be introduced into a body for a limited period of time, such as diagnostic and/or surgical devices, including endoscopes and minimally-invasive surgical tools. Such medical devices may include one or more functionalities at the distal end of the medical carriers, such as visualization elements (for example a camera), tissue modifies (for example, a cutter or electrode) etc.

Systems

Systems that include medical carriers of the invention are also provided. Systems of the invention include a medical carrier of the invention operatively coupled to a second device, such as a control unit. The control unit of systems of the invention may vary widely depending on the particular nature of the system, and may be present in an implantable structure or in an extra-corporeal device. The control unit may include a central processing unit (CPU) for controlling the functions of the system, and can also include programming, i.e., software, that can be run by the control unit. Examples of implantable control units of interest include implantable pulse generators, such as, but not limited to, pacemakers, defibrillators, etc. Examples of extra-corporeal control units of interest include extra-corporeal devices that provide for operation of effectors on the carrier, display data to a user (for example where the medical carrier is an endoscope and the data is displayed in the form of one or more images), etc. Medical carriers of the invention may be employed in a variety of different types of medical systems, including but not limited to: cardiac, neurological, muscular, gastrointestinal, skeletal, or pulmonary medical systems.

Figure 9:
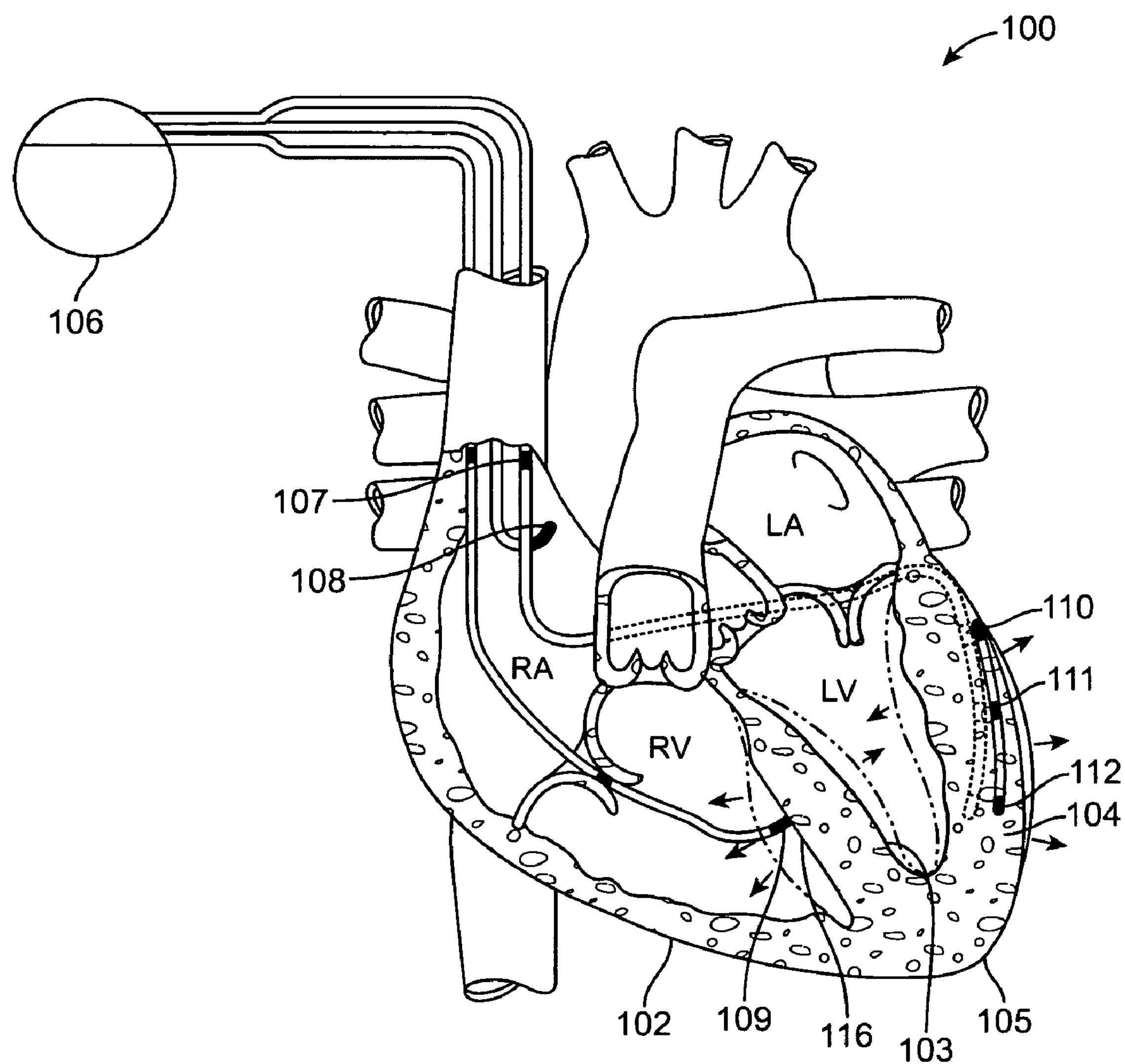
FIG. 9 shows a view of a heart with an embodiment of a cardiac resynchronization therapy (CRT) system that includes a medical carrier in accordance with the present invention.

A system that includes a medical carrier of the invention is depicted in FIG. 9. FIG. 9 provides a view of a heart having associated therewith a cardiac resynchronization therapy (CRT) system, where the leads (107, 108 and 109) of the system are medical carriers that include a low-impedance conductor, such as described above. The depicted system 100 includes control unit in the form of a pacemaker can 106, a first medical carrier which is a right ventricle electrode lead 109, a second medical carrier which is a right atrium electrode lead 108, and a third medical carrier which is left ventricle cardiac vein lead 107. Also shown are the right ventricle lateral wall 102, interventricular septal wall 103, apex of the heart 105, and a cardiac vein on the left ventricle lateral wall 104. The left ventricle electrode lead 107 has multiple effectors in the form of segmented electrodes 110, 111 and 112. Having multiple effectors allows a choice of optimal electrode location for CRT. The proximal end of left ventricle cardiac vein lead 107 connects to a pacemaker 106, which is the control unit of the system. The right ventricle electrode lead 109 is placed in the right ventricle of the heart with an active fixation helix 116 which is embedded into the cardiac septum.

Additional systems that may be modified to include medical carriers of the invention include, but are not limited to, those systems described in PCT application serial no. PCT/US2003/039524 published as WO/2004/052182; PCT application serial no. PCT/US2005/031559 published as WO/2006/029090; PCT application serial no. PCT/US2005/046811 published as WO/2006/069322; PCT application serial no. PCT/US2005/046815 published as WO/2006/069323; PCT application serial no. PCT/US2006/034258 published as WO/2007/028035; PCT application serial no. PCT/US2006/048944 published as WO/2007/075974; PCT application serial no. PCT/US2007/009270 published as WO/2007/120884; and PCT application serial no. PCT/US2007/014509 published as WO/2007/149546; the disclosures of which are herein incorporated by reference.

Fabrication Methods

Aspects of the subject invention also include a method of making medical carriers of the invention. In some instances, the methods of making medical carriers of the invention include providing a substrate and then producing the medical carrier from the substrate. In some instances, the low-impedance conductors are made from a monolithic substrate. As used herein, the terms "monolith" and "monolithic" refer to a substrate that is a single contiguous substrate. Producing the low-impedance conductors from a monolithic substrate can minimize defect sites, thus increasing the fatigue strength of the conductor. The substrates can be made from a variety of materials, where the materials can provide for the desired conductivity, corrosion resistance and biocompatibility for the conductors. In certain embodiments, the conductors can be fabricated from platinum or a platinum alloy, including, but not limited to platinum, 5% iridium; platinum, 10% iridium; platinum, 20% iridium; etc. Additionally, other platinum alloys may be used such as, but not limited to: platinum, 8% tungsten; platinum-nickel, platinum-rhodium, and the like. In some cases, the low-impedance conductors can comprise titanium or titanium alloys. Titanium may facilitate corrosion resistance, especially since titanium can be plated with platinum or the platinum alloys previously described. Other corrosion resistant alloys may be deposited by RF Sputtering, E beam vapor deposition or chemical vapor deposition, and other deposition methods. Additionally, the low-impedance conductors can comprise other materials, such as, but not limited to, stainless steel, cobalt based supper alloys, such as MP35N® alloy, or tantalum.

In some instances, the low-impedance conductors are made from a substrate, where the substrate may be a tubular substrate. Production of the low-impedance conductors from the provided substrate may include cutting the low-impedance conductor from the tubular substrate. The low-impedance conductors can be cut from the tubular substrate by any of a variety of convenient methods, such as, but not limited to, laser cutting, water-jet cutting, mechanical cutting, and the like. In certain instances, the methods include etching the low-impedance conductor from the tubular substrate. The low-impedance conductors can be etched from the tubular substrate by any convenient etching method, such as, but not limited to, chemical etching, electrochemical etching, photo etching, photochemical etching, and the like. Other methods of cutting and etching may include, but are not limited to, electric discharge machining (EDM), electroforming, stamping and forming, as well as a combination of these fabrication processes.

Alternatively, the provided substrate is substantially flat. In these instances, production of the low-impedance conductors may include cutting the low-impedance conductor from the substrate. Where desired, the low-impedance conductor cut from the subject may be shaped to provide a curved configuration, as described above. In such instances, shaping may be achieved using any convenient protocol, such as bending the low-impedance conductor about a mold of suitable shape, such as a cylinder.

Where desired, the substrate material can be of a cold worked condition comprising a refined microstructure formed by cold working. Refined microstructures can facilitate an increase in the yield point of the material and the fatigue life of the material.

In addition, the low-impedance conductors can include connectors along the length of the conductor. These connectors on the conductor can be produced during the cutting or etching process to allow for electrical connections and physical attachments along the length of the conductor.

After the conductor is cut or etched from the substrate, the conductor can be chemically etched or polished (for example, electropolished) to produce a smooth surface. Smooth surfaces may be desirable for fatigue resistant devices to reduce the number of potential crack initiation sites and to reduce residual stress in the material. In addition to polishing, the surface of the conductors can be treated by a variety of treatment methods. For example, the surface that is exposed to bodily fluids, such as the blood stream, can be treated to survive corrosion and electrolytic corrosion that occurs in that environment. In addition, the surface of the conductor can be treated to maximize the electric charge transfer to the target tissue. The surface of the conductor, in certain embodiments, can be treated to facilitate the sensing of electrical signals, chemical species or pH changes. Surface treatments imparting the above properties can include treatment with elements in the noble metal family, including the alloys, oxides and nitrides of noble metals.

Methods of making medical carriers in accordance with the invention may also include temperature treating (such as heat treating or chilling) the low-impedance conductors. Temperature treating can be performed prior to or after the conductor is produced from the substrate (for example prior to or after the cutting or etching process) and can facilitate setting the shape of the low-impedance conductor and increasing the yield strength and consequently the fatigue resistance of the low-impedance conductor. In some cases, temperature treating includes heating or chilling of the conductor to achieve a desired result such as hardening or softening of the conductor material. Additional aspects of the subject methods include hermetically sealing at least a portion of the low-impedance conductor. As used herein, the terms "hermetic seal" and "hermetically sealed" refer to airtight seals. Hermetic seals may be used to seal electronics against the undesired entry of liquids, microorganisms, gases, and the like. Thus, in certain embodiments, the subject conductors can be protected from corrosion by long term contact with saline, blood or other body fluid. Protocols for hermetically sealing the low-impedance conductors include, but are not limited to, those described in PCT application serial no PCT/US2007/009270 published under publication no. WO/2007/120884, the disclosure of which is herein incorporated by reference.

Furthermore, in some cases, methods of invention may include electrically connecting an effector to the low-impedance conductor. As described in detail above, the effector can comprise an electrode, where, in some cases, the effector is a segmented electrode comprising a processor and two or more electrodes. The effector can be electrically connected to the conductor in any of a variety of ways, such as, but not limited to, direct contact, soldering, clipping, crimping, etc.

In addition, in embodiments where the low-impedance conductor is configured to define a central lumen, as described above, the method can further include providing a polymer in the central lumen. The polymer can be pre-formed and then inserted into the central lumen, or formed in-situ, for example by injecting the polymer into the central lumen. As desired, the low impedance conductors may be incorporated into a polymeric sheath (such as a medical grade urethane sheath), using any convenient protocol.

Utility

Medical carriers of the invention find use in a variety of different devices and applications where it is desirable to provide a flexible conductor that has fatigue resistance, while minimizing the impedance of the conductor. Applications of interest include, but are not limited to, applications where the medical carrier is employed in conjunction with an implantable medical device, such as implantable pulse generator (for example pacemakers, implantable defibrillators, etc.); medical devices that can be inserted into the body of a subject, such as endoscopes; and the like. Medical devices in which the low-impedance conductors find use include those where flexibility and fatigue resistance are desired. Embodiments of the low-impedance conductors require minimal volume of the medical carriers with which they are associated, and therefore find use in medical carriers where small size, such as 12 Fr or less, including 3 Fr or less, is desired, and yet space for additional components, such as actuators, optical fibers, irrigation lumens, data conveyers, and the like is also desired.

Additionally, medical carriers of the invention find use high-frequency applications. High impedance and inductance can adversely affect high-frequency signals in terms of delay, range of operational frequency, signal to noise ratio and gain. Furthermore, high inductance may heat the conductor to a temperature causing tissue burns if, for example, the subject has an MRI. Thus, the subject medical carriers find use in applications where it is desirable to use conductors that have low-impedance.

Methods of using the medical carriers of the invention may vary depending on the particular nature of the medical carrier. During use, the medical carrier will be contacted with target body tissue, such as internal target body tissue. The specific type of target tissue may vary, where target tissues of interest include cardiac tissue, non-cardiac muscle tissue, nerve tissue, including peripheral and central nervous tissue, and the like. The method by which the carrier is contacted with the tissue may vary. For example, where the medical carrier is configured to be implanted into a subject, contact will be accomplished by way of an implantation protocol, such as an open-body or minimally invasive surgical protocol. Where the medical carrier is part of a diagnostic medical device, such as an endoscope, contact with target tissue may involve inserting the medical carrier at least partially into a body. Medical carriers of the invention may be employed with a variety of subjects, such as "mammals", where this term is used broadly to describe organisms which are within the class mammalia, including the orders carnivore (such as dogs and cats), rodentia (such as mice, guinea pigs, and rats), and primates (such as humans, chimpanzees, and monkeys).

In using the medical carriers of the invention, a signal is transmitted via the low-impedance conductor from a first position to a second position of a medical carrier. The nature of the transmitted (in other words sent for forwarded) along the low-impedance conductor may vary. In some instances, the signal is a power signal that delivers power to the second location of the medical carrier, e.g., to an effector positioned at the second location. In some instances, the signal is an information signal, where the information signal may include a variety of different types of information, such as but not limited to, configuration data, effector obtained data (such as physiological data), and the like.

Methods in which medical carriers of the invention may be employed are further described in PCT application serial no. PCT/US2003/039524 published as WO/2004/052182; PCT application serial no. PCT/US2005/031559 published as WO/2006/029090; PCT application serial no. PCT/US2005/046811 published as WO/2006/069322; PCT application serial no. PCT/US2005/046815 published as WO/2006/069323; PCT application serial no. PCT/US2006/034258 published as WO/2007/028035; PCT application serial no. PCT/US2006/048944 published as WO/2007/075974; PCT application serial no. PCT/US2007/009270 published as WO/2007/120884; and PCT application serial no. PCT/US2007/014509 published as WO/2007/149546; the disclosures of which are herein incorporated by reference.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A medical carrier comprising:

a lumen;

an insulating member formed on an outer surface of the lumen; and a first low-impedance conductor in contact with an outer surface of the insulating member, the first low-impedance conductor comprising a first longitudinally extended region configured as a first non-coiled repetitive pattern that imparts a fatigue resistance to the first longitudinally extended region, wherein the insulating member insulates each electrical component present in the lumen from the first low-impedance conductor.

2. The medical carrier according to claim 1, wherein the first longitudinally extended region is curved about a longitudinal axis.

3. The medical carrier according to claim 2, wherein the first longitudinally extended region comprises a radius of curvature of 10 mm or less about the longitudinal axis.

4. The medical carrier according to claim 2, wherein the first longitudinally extended region comprises an arc of 180 degrees or less about the first longitudinal axis.

5. The medical carrier according to claim 1, wherein the first non-coiled repetitive pattern comprises an irregular wave pattern.

6. The medical carrier according to claim 1, wherein the first low-impedance conductor comprises a resistance ranging from 0.01 Ω/cm to 5 Ω/cm.

7. The medical carrier according to claim 1, wherein the first low-impedance conductor comprises a bending stiffness ranging from 1 gram/cm per radian to 454 gram/cm per radian.

8. The medical carrier according to claim 1, wherein the first low-impedance conductor comprises a stretch ratio ranging from 0.2% to 20%.

9. The medical carrier according to claim 1, wherein the first longitudinally extended region has a length of 100 mm or less.

10. The medical carrier according to claim 9, wherein the first longitudinally extended region has a length of 10 mm or greater.

11. The medical carrier according to claim 1, further comprising a second low-impedance conductor comprising a second longitudinally extended region configured as a second non-coiled repetitive pattern that imparts a fatigue resistance to the second longitudinally extended region, wherein a frequency of the first non-coiled repetitive pattern is different from a frequency of the second non-coiled repetitive pattern.

12. The medical carrier according to claim 1, further comprising an effector electrically coupled to the first low-impedance conductor.

13. The medical carrier according to claim 12, wherein the effector comprises an electrode.

14. The medical carrier according to claim 13, wherein the effector is a segmented electrode comprising a processor and two or more electrodes.

15. The medical carrier according to claim 1, further comprising two or more longitudinally spaced effectors separated by the first longitudinally extended region.

16. The medical carrier according to claim 1, further comprising a proximal end connector configured to operably couple the first low-impedance conductor to an additional conductive element.

17. A system comprising:

a control unit; and a medical carrier coupled to the control unit, the medical carrier comprising:

a lumen;

an insulating member formed on an outer surface of the lumen; and a first low-impedance conductor in contact with an outer surface of the insulating member, the first low-impedance conductor comprising a first longitudinally extended region configured as a first non-coiled repetitive pattern that imparts a fatigue resistance to the first longitudinally extended region, wherein the insulating member insulates each electrical component present in the lumen from the first low-impedance conductor.

18. The system according to claim 17, wherein the control unit comprises an implantable pulse generator.

19. The system according to claim 18, further comprising an effector electrically connected to the first low-impedance conductor.

20. The system according to claim 19, wherein the effector comprises an electrode.

21. The system according to claim 20, wherein the effector is a segmented electrode comprising a processor and two or more electrodes.

22. A method of making a medical carrier, the method comprising:

providing a substrate; and producing the medical carrier from the substrate, wherein the medical carrier comprises:

a lumen;

an insulating member formed on an outer surface of the lumen; and a first low-impedance conductor in contact with an outer surface of the insulating member, the first low-impedance conductor comprising a first longitudinally extended region configured as a first non-coiled repetitive pattern that imparts fatigue resistance to the first longitudinally extended region, wherein the insulating member insulates each electrical component present in the lumen from the first low-impedance conductor.

23. The method according to claim 22, wherein the substrate comprises a tubular substrate and the producing comprises cutting or etching the first low-impedance conductor from the tubular substrate.

24. The method according to claim 22, wherein the substrate is substantially flat and wherein the producing comprises:

cutting the first low-impedance conductor from the substrate; and bending the first low-impedance conductor around a longitudinal axis.

25. The method according to claim 22, further comprising electrically connecting an effector to the first low-impedance conductor.

* * * * *